(12) United States Patent
Tsuji et al.

(10) Patent No.: US 11,382,939 B2
(45) Date of Patent: *Jul. 12, 2022

(54) COMPOSITION WHICH CONTAINS LACTIC ACID BACTERIUM AS EFFECTIVE COMPONENT AND WHICH IS FOR PREVENTING OR AMELIORATING SKIN CONDITION DETERIORATION CAUSED BY ABNORMAL PROLIFERATION OF SPECIFIC BACTERIUM IN SKIN

(71) Applicant: Kirin Holdings Kabushiki Kaisha, Tokyo (JP)

(72) Inventors: Ryohei Tsuji, Tokyo (JP); Toshio Fujii, Tokyo (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 176 days.

This patent is subject to a terminal disclaimer.

(21) Appl. No.: 16/333,548

(22) PCT Filed: Sep. 7, 2017

(86) PCT No.: PCT/JP2017/032330
§ 371 (c)(1),
(2) Date: Mar. 14, 2019

(87) PCT Pub. No.: WO2018/051895
PCT Pub. Date: Mar. 22, 2018

(65) Prior Publication Data
US 2020/0179463 A1 Jun. 11, 2020

(30) Foreign Application Priority Data

Sep. 15, 2016 (JP) .............................. JP2016-180851

(51) Int. Cl.
*A61K 35/744* (2015.01)
*A61P 17/00* (2006.01)
*A23L 33/135* (2016.01)
*A61K 9/00* (2006.01)

(52) U.S. Cl.
CPC .......... *A61K 35/744* (2013.01); *A23L 33/135* (2016.08); *A61K 9/0053* (2013.01); *A61P 17/00* (2018.01); *A23Y 2240/41* (2013.01)

(58) Field of Classification Search
CPC .................................................. A61K 35/744
See application file for complete search history.

(56) References Cited

U.S. PATENT DOCUMENTS

| 2008/0226603 A1 | 9/2008 | Al-Ghazzewi et al. |
| 2008/0233091 A1 | 9/2008 | Ross et al. |
| 2009/0214497 A1 | 8/2009 | Park et al. |
| 2009/0317370 A1 | 12/2009 | Lang et al. |
| 2014/0065218 A1 | 3/2014 | Lang et al. |
| 2014/0186409 A1 | 7/2014 | Lang et al. |
| 2015/0079040 A1 | 3/2015 | O'Neill et al. |
| 2015/0366920 A1* | 12/2015 | Desroche ............... A61K 45/06 424/463 |
| 2017/0189458 A1* | 7/2017 | Kanayama ............. A61K 39/39 |
| 2021/0008127 A1* | 1/2021 | Tsuji .................... A61K 35/744 |

FOREIGN PATENT DOCUMENTS

| JP | 2002-171933 A | 6/2002 | |
| JP | 2003-259860 A | 9/2003 | |
| JP | 2007-537224 A | 12/2007 | |
| JP | 2014-513106 A | 5/2014 | |
| JP | 5495559 B2 | 5/2014 | |
| JP | 2015-514127 A | 5/2015 | |
| JP | 5826241 B2 | 12/2015 | |
| JP | 2016-508712 A | 3/2016 | |
| JP | 5916846 B2 | 5/2016 | |
| WO | WO-2010/013179 A1 | 2/2010 | |
| WO | WO2010013179 A1 * | 2/2010 | ............. A61Q 19/00 |
| WO | WO-2015182735 A1 * | 12/2015 | ........... A23L 33/135 |
| WO | WO-2017/025936 A2 | 2/2017 | |

OTHER PUBLICATIONS

Jounai K, et al. Oral administration of *Lactococcus lactis* subsp. *lactis* JCM5805 enhances lung immune . . . PLoS One. Mar. 6, 2015; 10(3):e0119055. (Year: 2015).*
Cui Y et al. (2016) Different Effects of Three Selected Lactobacillus Strains in Dextran Sulfate Sodium-Induced Colitis in BALB/c Mice. PLoSONE 11(2): e0148241. (Year: 2016).*
Fujiwara D et al. (2004) The anti-allergic effects of lactic acid bacteria are strain dependent and mediated by effects on both Th1/Th2 cytokine expression and balance. Int Arch Allergy Immunol. Nov. 2004;135(3):205-15. (Year: 2004).*
Fujiwara D et al. (2005) A Double-blind Trial of Lactobacillus paracasei Strain KW3110 Administration for Immunomodulation in Patients with Pollen Allergy. Allergology International. 2005; 54:143-49. (Year: 2005).*
Genus *Lactococcus*. Bacterio.net. Accessed Oct. 18, 2020. https://www.bacterio.net/genus/lactococcus. (Year: 2020).*
Rademaker et al. (2007) Diversity analysis of dairy and nondairy Lactococcus lactis isolates, using a novel multilocus sequence analysis scheme and (GTG)5-PCR fingerprinting. Applied and environmental microbiology vol. 73, 22: 7128-37. (Year: 2007).*
Todar K. (Aug. 3, 2016). Todar's online textbook of bacteriology, http://textbookofbacteriology.net. (Year: 2016).*
Yan S et al. (Jan. 2016) *Lactococcus nasutitermitis* sp. nov. isolated from a termite gut. Int J Syst Evol Microbiol. Jan. 2016;66(1):518-522. (Year: 2016).*
Yun X et al. (May 2018). Effects of dietary Lactobacillus rhamnosus JCM1136 and *Lactococcus lactis* subsp. *lactis* JCM5805 on the growth, . Fish & Shellfish Immunology. 3018 May 76:368-79. (Year: 2018).*

(Continued)

*Primary Examiner* — Vera Afremova
(74) *Attorney, Agent, or Firm* — Foley & Lardner LLP (57) ABSTRACT

Provided is a pharmaceutical composition and food composition for treating or preventing a skin disease caused by abnormal growth of a skin bacterium or infection with a pathogenic microorganism. A composition comprising a lactic acid bacterium as an active ingredient, for suppressing bacterial abnormal growth, or preventing or ameliorating deterioration of skin condition caused by a bacterial abnormal growth, by oral intake thereof.

16 Claims, 7 Drawing Sheets

Specification includes a Sequence Listing.

(56) References Cited

OTHER PUBLICATIONS

Michel T et al. (Dec. 5, 2012)/ Mouse lung and spleen natural killer cells have phenotypic and functional differences . . . PLoS One. 2012;7(12):e51230. doi: 10.1371/journal.pone.0051230. Epub Dec. 5, 2012. Erratum in: PLoS One. 2013;8(1). (Year: 2012).*

Ohashi, Y. and Ushida, K. (2009) Health-beneficial effects of probiotics: Its mode of action. Animal Science Journal, (2009) 80: 361-371. doi: 10.1111 /j. 1740-0929.2009.00645.x (Year: 2009).*

Specialty Feeds Brochure. (2014). Standard AIN93G Rodent Diet. Aug. 14, 2014. https://www.specialtyfeeds.com/new/wp-content/uploads/2016/06/sf_ain93g.pdf (accessed Oct. 23, 2020) (Year: 2014).*

Supplementary European Search Report dated Mar. 26, 2020 in EP 17850798.4.

Charlier et al., "Acidification is not involved in the early inhibition of *Staphylococcus aureus* growth by Lactococcus lactis in milk," International Dairy Journal, 2008, vol. 18, pp. 197-203.

Kobayashi et al., "Dysbiosis and *Staphylococcus aureus* Colonization Drives Inflammation in Atopic Dermatitis," Immunity, 2015, vol. 42, 99.756-766.

International Search Report dated Oct. 10, 2017, in PCT/JP2017/032330.

* cited by examiner

SEQUENCE LISTING

<160> NUMBER OF SEQ ID NOS: 10

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
aacgacccct tcattgac                                              18

<210> SEQ ID NO 2
<211> LENGTH: 19
<212> TYPE: DNA
<213> ORGANISM: Artificial
<220> FEATURE:
<223> OTHER INFORMATION: primer -continued

<400> SEQUENCE: 2
tccacgacat actcagcac                                          19

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ggaaatcacc atgccctcta                                         20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gctgtctttg tgagatgcca                                         20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ccagatggag ccaggtgttg                                         20

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
agctggagcg gagacagaat cc                                      22

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
gcattggcaa cactcgtcag a                                       21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
cgggatcttg gtcttctcta                                         20

```
<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
tcttgttctt ggtgcctgct                                               20

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
cgaccgctat tagaacatcg ac                                            22
```

COMPOSITION WHICH CONTAINS LACTIC ACID BACTERIUM AS EFFECTIVE COMPONENT AND WHICH IS FOR PREVENTING OR AMELIORATING SKIN CONDITION DETERIORATION CAUSED BY ABNORMAL PROLIFERATION OF SPECIFIC BACTERIUM IN SKIN

CROSS-REFERENCE TO RELATED APPLICATIONS

This application is the U.S. National Stage of PCT/JP2017/032330, filed Sep. 7, 2017, which claims priority to JP 2016-180851, filed Sep. 15, 2016.

The instant application contains a Sequence Listing which has been submitted in ASCII format via EFS-WEB and is hereby incorporated by reference in its entirety. Said ASCII copy, created on Mar. 12, 2019, is named sequence.txt and is 3 KB.

TECHNICAL FIELD

The present invention is a composition containing a lactic acid bacterium and exerting a therapeutic or prophylactic effect on a skin disease caused by abnormal growth of a bacterium transmitted to the skin to deteriorate skin condition or bacterial infection, by oral intake of the composition.

BACKGROUND ART

Humans are always in contact with a great many microorganisms in daily life. Particularly, the skin, which is always in contact with external environment, is more frequently exposed to a risk of infection with pathogenic microorganisms, compared to other tissues. A wide variety of microorganisms specific to the skin also reside on the skin and these microorganisms are collectively called as resident bacterial flora. Recently, the balance of resident bacterial flora and homeostasis of the skin has been aggressively studied and skin condition is found to deteriorate if a specific bacterium abnormally grows. If infection with a pathogenic microorganism occurs or if a specific bacterium abnormally grows, symptoms such as eczema, rough skin, swelling, blister and bleeding are observed, and itching and pain occur. Particularly when infectious skin roughness occurs at a site such as a face that can be seen well by others, QOL (quality of life) of the infected person markedly decreases. Recently, in specific skin diseases (e.g., atopic dermatitis), it is also suggested that abnormal growth of *Staphylococcus aureus* may be connected with exacerbation of clinical symptoms (see, Non Patent Literature 1). Likewise, even in skin diseases that had not been known for its connection with infections, it has also been suggested that a risk such as bacterial transmission and abnormal growth is strongly connected with skin diseases.

Since a treatment for a skin infection differs between a bacterial infection and a viral infection, diagnosis for the causative microorganism is important. In the case of a bacterial infection, an antibiotics substance is principally administered for treatment. However, heavy use of the antibiotic substance has a risk for emerging a resistant bacterium. In the case of a viral infection, since existing antiviral drugs act only on limited viral species, the treatment is nothing more than a symptomatic therapy.

Because of this, an idea that attracts attention is preventing a bacterial infection by enhancing the barrier function of keratinocytes of the skin. It has been confirmed that *Lactobacillus rhamnosus, Lactobacillus reuteri* and *Bifidobacterium longum* have such an effect (see, Patent Literature 1). Another idea that attracts attention is controlling skin bacterial flora by a specific organism co-present on the skin, thereby successfully promoting healthy conditions or inhibiting a disease. A lactic acid bacterium belonging to the genus *lactobacillus* is known to aggregate with *Streptococcus pyogenes* to effectively inhibit growth of *Streptococcus pyogenes* (see, Patent Literature 2). For example, it is known that lactic acid bacteria, such as *Lactobacillus delbrueckii* (see Patent Literature 3) and *Lactobacillus buchneri* (see Patent Literature 4), bind to transient pathogenic skin bacteria and inhibit their growth, thereby suppressing bacterial infection. It is also known that *Lactobacillus saniviri, Lactobacillus salivarius* and *Lactobacillus pentosus* adhere to *Staphylococcus aureus, Pseudomonas aeruginosa, pyogenic streptococcus* to inhibit their growth (see Patent Literature 5). However, all lactic acid bacteria exhibit their functions only by direct application onto the skin and it is actually impossible to always keep on applying these lactic acid bacteria on the whole body. For the reason, it has been desired to develop a method for more simply preventing/treating infections of the skin of the whole body.

CITATION LIST

Patent Literatures

Patent Literature 1: JP Patent Publication (Kohyo) No. 2015-514127 A
Patent Literature 2: JP Patent No. 5916846
Patent Literature 3: JP Patent No. 5495559
Patent Literature 4: JP Patent No. 5826241
Patent Literature 5: JP Patent Publication (Kohyo) No. 2016-508712 A

Non Patent Literature

Non Patent Literature 1: Kobayashi T et al., (2015) Immunity. 42, 4, 756-766

SUMMARY OF INVENTION

Technical Problem

An object of the present invention is to provide a food composition and a pharmaceutical composition for preventing or ameliorating deterioration of skin condition caused by abnormal growth of a specific bacterium, by oral intake of the composition comprising a lactic acid bacterium.

Solution to Problem

The present inventors intensively studied on whether or not deterioration of skin condition caused by abnormal growth of a specific bacterium can be reduced by oral intake of a lactic acid bacterium.

As a result, the inventors have found that growth of *Staphylococcus aureus*, which was applied to the skin to infect the skin therewith, and deterioration of skin condition can be prevented by oral intake of a lactic acid bacterium. Based on the findings, the present invention has been achieved.

More specifically, the present invention is as follows.

[1] A composition comprising a lactic acid bacterium as an active ingredient, for suppressing abnormal growth of a bacterium, or preventing or ameliorating deterioration of skin condition caused by abnormal growth of a bacterium, by oral intake thereof.

[2] The composition according to [1], wherein the bacterium is selected from the group consisting of *Staphylococcus aureus, Staphylococcus epidermidis*, group-A β-hemolytic streptococcus (*Streptococcus pyogenes*), *Pseudomonas aeruginosa*, fluorescent diphtheroid and rod-shape acne (*Propionibacterium acnes*).

[3] The composition according to [2], wherein the bacterium is selected from the group consisting of *Staphylococcus aureus, Staphylococcus epidermidis* and rod-shape acne (*Propionibacterium acnes*).

[4] The composition according to any one of [1] to [3], wherein the lactic acid bacterium belongs to the genus *Lactococcus*.

[5] The composition according to any one of [1] to [3], wherein the lactic acid bacterium is *Lactococcus lactis*.

[6] The composition according to any one of [1] to [3], wherein the lactic acid bacterium is *Lactococcus lactis* JCM5805 strain.

[7] The composition according to any one of [1] to [6], being a food composition.

[8] The composition according to any one of [1] to [6], being a pharmaceutical composition.

[9] The composition according to [7] or [8], wherein the skin condition caused by abnormal growth of the bacterium is rough skin or dermatitis.

[10] The composition according to [8], wherein the skin condition caused by abnormal growth of the bacterium is selected from the group consisting of impetigo contagiosa, cellulitis, erysipelas, staphylococcal scalded skin syndrome, folliculitis, acne, furuncle, carbuncle, bacterial perionychium inflammation, chronic pyoderma and sycosis vulgaris.

The specification incorporates the contents described in the specification and/or drawings of JP Patent Application No. 2016-180851 based on which the present application claims for priority.

Advantageous Effects of Invention

Owing to the present invention, it is possible to provide a food composition and a pharmaceutical composition exerting a suppression effect on specific-bacterium abnormal growth in the skin, thereby preventing or ameliorating deterioration of skin condition, by oral intake of a lactic acid bacterium.

DESCRIPTION OF EMBODIMENTS

Now, the present invention will be more specifically described below.

The present invention is a composition comprising a lactic acid bacterium as an active ingredient, for preventing or ameliorating deterioration of skin condition caused by abnormal growth of a specific bacterium.

Examples of the deterioration of skin condition caused by bacterial abnormal growth include rough skin, swelling and eczema, and further include a pathological condition of the skin exacerbated by infection with a pathogenic bacterium. The composition of the present invention can reduce or suppress exacerbation of a pathological change of the skin caused by infection of the skin with a pathogenic bacterium.

Examples of the pathological change of the skin include papule and erosion on the skin; scab, epidermal thickening, pustule, erosion/ulceration, intercellular edema and intracellular edema on the epidermis; and inflammatory cell infiltration on the dermis and subcutaneous tissue. The composition of the present invention reduces the severity of these pathological changes.

The skin condition caused by bacterial abnormal growth includes a skin disease developed by infection with a pathogenic bacterium. The skin disease developed by infection with a pathogenic bacterium is also referred to as a skin infection caused by a pathogenic bacterium. The skin disease is preferably a rough skin with inflammation or dermatitis.

More specifically, the present invention is a composition comprising a lactic acid bacterium as an active ingredient, for suppressing or preventing deterioration of skin condition caused by abnormal growth of a specific bacterium, i.e., a composition for treating or preventing a skin infection with a pathogenic bacterium.

Examples of a bacterium causing abnormal growth or deterioration of skin condition include bacteria belonging to the genus *staphylococcus* such as *Staphylococcus aureus* and *Staphylococcus epidermidis*; bacteria belonging to the genus *streptococcus* such as group-A β-hemolytic streptococcus (*Streptococcus pyogenes*); bacteria belonging to the genus *Pseudomonas* such as *Pseudomonas aeruginosa*; bacteria belonging to the genus *corynebacterium* such as fluorescent diphtheroid; and bacteria belonging to the genus *propionibacterium* such as *Propionibacterium acnes*. The composition of the present invention can be used for suppression, treatment or prevention of deterioration of skin condition caused by abnormal growth of these bacteria or transmission of them, and particularly preferably can be used for suppression, treatment or prevention of deterioration of skin condition caused by *Staphylococcus aureus*. However, the effect against deterioration of skin condition caused by abnormal growth of *Staphylococcus aureus*, is an example, and the effect is not limited to that against *Staphylococcus aureus* alone.

As the skin disease that can be treated or prevented by the composition of the present invention, the following diseases are mentioned. In the following, names of skin diseases and causative bacteria are shown; however, the following skin diseases are just examples, the skin diseases are not limited to these.

Impetigo Contagiosa
Blister-like *Staphylococcus aureus*
Encrusted group-A β-hemolytic *streptococcus*
Cellulitis
*Staphylococcus* or group-A β-hemolytic *streptococcus*
Erysipelas
Group-A β-hemolytic *streptococcus*
SSSS: Staphylococcal Scalded Skin Syndrome
*Staphylococcus aureus*
Folliculitis (follicular inflammation)
*Staphylococcus aureus* and *Staphylococcus epidermidis*
Acne (acne vulgaris)
Acne is a kind of folliculitis and occurs on a youngster's face.
*Staphylococcus aureus, Staphylococcus Epidermidis* and Rod-Shape Acne
Furuncle (boil) and carbuncle
Furuncle and carbuncle refer to advanced state of folliculitis.
*Staphylococcus aureus* and *Staphylococcus epidermidis*
Bacterial perionychium inflammation
*Staphylococcus aureus*, group-A β-hemolytic *streptococcus* and *Pseudomonas aeruginosa*
Multiple sweat gland abscess (staphylococcal periporitis)
*Staphylococcus aureus*
Chronic pyoderma
*Staphylococcus aureus* and *Staphylococcus epidermidis*
Sycosis vulgaris (razor burn)
*Staphylococcus aureus* and *Staphylococcus epidermidis*
Erythrasma
Fluorescent diphtheroid The symptom of atopic dermatitis is reported to worse by infection with *Staphylococcus aureus*, and the composition of the present invention can be used for reduction and amelioration of the symptom of atopic dermatitis.

*Lactococcus lactis* JCM5805 mentioned above can be obtained from the RIKEN BioResource Research Center (3-1-1, Koyadai, Tsukuba-shi, Ibaraki, Japan). An equivalent strain to *Lactococcus lactis* JCM5805 can be used. The equivalent strain herein refers to a strain derived from *Lactococcus lactis* JCM5805, an original strain from which *Lactococcus lactis* JCM5805 is derived or a descendant strain of the original strain. The equivalent strain is sometimes stored in another culture collection. Examples of the culture collection include, but are not limited to, the American Type Culture Collection (USA) and Culture Collection Room of Tokyo University of Agriculture, (1-1-1 Sakuragaoka, Setagaya-ku, Tokyo, Japan).

The composition of the present invention contains a culture of a lactic acid bacterium as mentioned above. The culture refers to living cells, dead cells, a disrupted material of living cells or dead cells, a lyophilizate of living cells or dead cells, a disrupted material of the lyophilizate, a culture solution and a culture-solution extract, and includes part of a lactic acid bacterial cell and a treated lactic acid bacterial cell. Further, DNA or RNA of the lactic acid bacterium is included in the culture of the lactic acid bacterium.

A lactic acid bacterium can be cultured by a method known in the art using a medium known well. As a medium, a commercially available medium for culturing a lactic acid bacterium such as MRS medium, GAM medium and LM17 medium, can be used. The medium, appropriately supplemented with additives such as an inorganic salt, a vitamin, an amino acid, an antibiotic substance and a serum, may be put in use. Culture may be carried out at 25 to 40° C. for several hours to several days.

After culture, lactic acid bacterial cells are collected by centrifugation or filtration. If dead lactic acid bacterial cells are used, the cells may be killed by, e.g., an autoclave.

Oral intake of the composition containing a lactic acid bacterium as mentioned above promotes and augments expression of an antibacterial gene (antimicrobial gene) in the skin to prevent or ameliorate deterioration of the skin condition caused by abnormal growth of a specific bacterium or infection with a pathogenic microorganism. A protein, which is an expression product of the antibacterial gene, binds to a bacterium and destroys the cell membrane to kill the bacterial cell. Examples of the antibacterial gene include β-defensin 1 (BD-1), β-defensin 3 (BD-3), β-defensin 14 (BD-14) and S100A8.

As the lactic acid bacterium that can be used as the active ingredient of the composition of the present invention, it is preferable to use a lactic acid bacterium exerting therapeutic or prophylactic effect on a skin infection of a living body even if it is orally taken. Such a lactic acid bacterium is highly resistant to gastric juice and intestinal fluid, in other words, has strong resistance to an acid and can be delivered live to the intestinal tract. *Lactococcus lactis* JCM5805 mentioned above can exert a therapeutic or prophylactic effect on a skin infection even if it is orally taken.

The composition of the present invention includes a food composition, more specifically, food and drink. The food composition can be used for preventing or ameliorating deterioration of the skin condition, such as rough skin, swelling and eczema, that is caused by abnormal growth of a specific bacterium or infection with a pathogenic microorganism mentioned above. Preventing or ameliorating deterioration of skin condition caused by abnormal growth of a specific bacterium or infection with a pathogenic microorganism refers to suppressing abnormal growth of a specific bacterium in the skin or infection with a pathogenic microorganism, thereby suppressing exacerbation of skin inflammation.

A lactic acid bacterium can be used as a food composition as it is or may be used as a component of a food and drink. The type of food and drink to be used is not particularly limited as long as an active ingredient, which is used for reducing or ameliorating the symptom of a skin disease caused by abnormal growth of a specific microorganism or infection with a pathogenic bacterium, is not inhibited. Examples of the food and drink that can be used include dairy products; beverages; seasonings; alcoholic beverages; agricultural and forestry processed products; confectioneries and breads; cereal flours and noodles; fishery processed products; livestock processed products; oils and fats, and processed products of these; prepared frozen foods; retort foods; instant foods; and food materials. Of them, fermented dairy products such as yogurt and cheese, lactic acid bacteria beverages or beverages such as soft drinks, non-alcoholic beverages and sports drinks, can be used. If a lactic acid bacterium is used in a fermented food and drink, lactic acid bacterial cells can be inactivated and added to a fermented food and drink in a requisite amount or can be used as a lactic acid bacterium starter to produce a fermented food and drink.

Examples of the food composition include dietary supplements and food additives.

Examples of the food and drink of the present invention include functional foods, health foods and drinks, specified health foods and drinks, nutritional function foods and drinks and health food and drink supplements. The specified health foods and drinks herein refer to foods and drinks that are allowed to display that they are taken as diets for special purpose for health reason and expected to attain the purpose for health reason. The functional foods are foods having functions that are supported by a scientific ground and displayed on its package under responsibility of a business operator (the display can be allowed by registering to the Consumer Affairs Agency).

A food composition containing a lactic acid bacterium may be orally taken for reducing or ameliorating the skin condition that was changed by abnormal growth of a specific microorganism or infection with a pathogenic bacterium. If the composition is orally taken in advance, it can suppress abnormal growth of a specific microorganism and infection of the skin with a pathogenic bacterium. Even if the skin is infected with a pathogenic microorganism, the food composition can suppress growth of the pathogenic bacterium. More specifically, the food composition can reduce and ameliorate the symptoms of a skin disease caused by abnormal growth of a specific microorganism or infection with a pathogenic bacterium and suppress exacerbation of a pathological change of the skin.

The composition of the present invention comprising a lactic acid bacterium as an active ingredient for treating or preventing a skin disease caused by infection with a pathogenic bacterium includes a pharmaceutical composition. The pharmaceutical composition can be used for treating or preventing the skin disease caused by infection with a pathogenic bacterium. The pharmaceutical composition can be used for reducing and ameliorating the symptoms of the skin disease caused by infection with a pathogenic bacterium and suppressing exacerbation of a pathological change of the skin caused by infection with a pathogenic bacterium.

The pharmaceutical composition may be referred to as a therapeutic or prophylactic agent for a skin disease caused by infection with a pathogenic bacterium, as an agent for reducing and ameliorating the symptoms of a skin disease caused by infection with a pathogenic bacterium or as an inhibitor of exacerbation of a pathological change of the skin caused by infection with a pathogenic bacterium.

Examples of the form of the pharmaceutical composition include, but are not particularly limited to, powder, granule, tablet and syrup. The pharmaceutical composition of the present invention is preferably administered orally. The pharmaceutical composition may contain an excipient, a disintegrant, a binder, a lubricant and a colorant. Examples of the excipient include glucose, lactose, cornstarch and sorbitol. Examples of the disintegrant include starch, sodium alginate, gelatin powder, calcium carbonate, calcium citrate and dextrin. Examples of the binder include dimethylcellulose, polyvinyl alcohol, polyvinyl ether, methylcellulose, ethylcellulose, gum Arabic, gelatin, hydroxypropylcellulose and polyvinylpyrrolidone. Examples of the lubricant include talc, magnesium stearate, polyethylene glycol and hydrogenated vegetable oil.

The dosage amount can be appropriately determined depending on the age, body weight and gender of the patient to be administered, the disease and severity of the symptom. The dosage amount is administered once a day or separated into several portions and administered several times a day. A culture may be administered in an amount equivalent to $1 \times 10^9$ to $1 \times 10^{12}$ bacterial cells per time. Alternatively, 1 to 1000 mg/time in terms of dry weight of lactic acid bacterial cells and preferably 20 to 300 mg/time may be administered.

The present invention encompasses a lactic acid bacterium for suppressing bacterial abnormal growth or preventing or ameliorating deterioration of skin condition caused by bacterial abnormal growth, by oral intake.

The present invention encompasses a method of suppressing bacterial abnormal growth or a method of preventing or ameliorating deterioration of skin condition caused by bacterial abnormal growth, comprising administrating a lactic acid bacterium.

The present invention further encompasses a method of suppressing bacterial abnormal growth or use of a lactic acid bacterium for producing a pharmaceutical composition for preventing or ameliorating deterioration of skin condition caused by bacterial abnormal growth.

EXAMPLES

The present invention will be more specifically described by way of Examples; however, the present invention is not limited by these Examples.

[Example 1] Preparation of *Staphylococcus aureus* Suspension

*Staphylococcus aureus* cells used in the present invention were prepared by the method as shown below.
<Experimental Method>
*Staphylococcus aureus* MX2 strain was obtained from the American Type Culture Collection (ATCC), which is a biological resources bank in USA. In each test, a nutrient broth medium (10 mL) (manufactured by Eiken Chemical Co., Ltd.) was added in a test tube, and then, a frozen bacterial suspension (100 μL) was thawed and inoculated to the medium. The medium was cultured in an isothermal shaking culture machine (manufactured by TAITEC CORPORATION) at 37° C. while shaking. After culture, the bacterial suspension was centrifugally separated (1000 rpm, 5 minutes) by a centrifuge and the supernatant was removed. To obtain an inoculum suspension stock, physiological saline (2 mL) was added to the bacterial precipitate and stirred.

The inoculum suspension stock was diluted with physiological saline and the turbidity of the diluted suspension was visually controlled in accordance with the McFarland turbidimetric method so as to obtain a turbidity of 1. An aliquot was taken from the bacterial suspension controlled to have McFarland 1 and diluted 100 fold with physiological saline to prepare an inoculum suspension.

The number of bacterial cells in the inoculum suspension was determined by taking an aliquot of the inoculum suspension, diluting it $10^3$ or $10^4$ fold with physiological saline, smearing the diluted suspension to an nutrient broth agar plate and culturing the medium in an incubator (MTR-251, SANYO Electric Co., Ltd.) set at 37° C. for 2 days, thereafter, counting the number of colonies by a pen-type colony counter, and calculating the number of living bacterial cells contained in the inoculum suspension (1 mL) to obtain a bacterial concentration (cfu/mL).
<Results>
The concentration of *Staphylococcus aureus* used in Example 2 was $3.4 \times 10^6$ cfu/mL and that in Example 3 was $3.0 \times 10^6$ cfu/mL.

[Example 2] Analysis on Protective Effect of *Lactococcus lactis* JCM5805 Against *Staphylococcus aureus* Epicutaneous Infection

*Staphylococcus aureus* was inoculated in the skin of mice allowed to orally take *Lactococcus lactis* JCM5805 and evaluation on the severity of pathological score, counting of the number of living *Staphylococcus aureus* cells, histopathological examination and determination of antibacterial genes expression were carried out. In this manner, the protective effect against bacterial infection was evaluated.

In the Example, the pathological score is sometimes called as a skin pathological severity or skin pathological score.

<Experimental Method>

BALB/C mice (5 weeks-old females, purchased from Japan SLC, Inc.) were divided into two groups each constituted of 16 mice. One was a standard diet intake group (AIN-93G diet manufactured by Oriental Yeast Co., Ltd). The other was a *Lactococcus lactis* JCM5805 intake group, which was fed AIN93G, mixed with *Lactococcus lactis* JCM5805. The dosage amount of the lactic acid bacterium per day per mouse was set to be 1 mg. The day on which administration of the lactic acid bacterium was initiated was specified as Day 0. On Day 14, the back of each mouse was shaved by an electric razor, and applied hair removal cream (Epilat®, Kracie Home Products Ltd.) to set an infection area having about 2 cm squares, and then striped three times with a cloth adhesive tape under anesthesia with ketamine hydrochloride (intramuscular administration, 2.0 mL/kg, ketamine hydrochloride injection; animal KETALAR® 50 injection solution; Bayer Yakuhin, Ltd.). On Day 15 after administration, the infection area was stripped again three times with a cloth adhesive tape under anesthesia with ketamine hydrochloride, and then, the inoculum suspension of *Staphylococcus aureus* was added dropwise by means of a micropipette in an amount of 0.1 mL ($3.4 \times 10^5$ cfu/head) per mouse.

On Day 17 corresponding to two days after *Staphylococcus aureus* inoculation suspension was inoculated, severity of pathological score of the infection area was evaluated. Individual mice were checked for papule and erosion of the infection area in accordance with the following 4 criteria: 0: asymptomatic, 1: mild, 2: moderate, 3: severe. The sum of evaluation scores on papule and erosion was used as a skin pathological score.

On Day 17, mice each were dissected and the whole infection area and an ear were collected. The samples of the infection area in 8 mice per group were subjected to determination of the number of living cells in the skin and those in the rest 8 mice were used as histopathological examination. The ear samples of all mice were used for antibacterial-gene expression analysis by quantitative PCR.

The number of living cells were determined as follows. The skin of the infection area sample was cut into pieces and homogenized in 2 mL of physiological saline by means of a stirrer to obtain a skin-tissue suspension. An aliquot was taken from the skin-tissue suspension and diluted with physiological saline up to an optimal concentration to obtain a skin-tissue diluent. The skin-tissue diluent (100 µL) was smeared onto a *staphylococcus* agar plate (manufactured by Eiken Chemical Co., Ltd.) by a bacteria spreader and cultured at 37° C. for 2 days. The number of colonies (cfu/head) contained in the whole infection area was calculated.

Histopathological examination was carried out by embedding the skin of the infection area sample in paraffin in accordance with a routine method and preparing HE (Hematoxylin-Eosin)-stained tissue preparations. The items examined were severities of scab, epidermal thickening, pustule, erosion/ulceration, intercellular edema and intracellular edema in the epidermis. In addition, the severities of inflammatory cell infiltration in the dermis and subcutaneous tissue were examined. Individual examination items were separately evaluated based on the 4 criteria: 0: asymptomatic, 1: mild, 2: moderate, 3: severe.

The ear samples each were cut into pieces by a Multi Beads Shocker, and then, suspended with TRIzol (manufactured by Life Technologies Corporation) and centrifuged. The aqueous layer was taken and isopropanol precipitation was carried out, and then, the precipitate was suspended in RNase-free water. In this manner, total RNA was extracted. RNA was purified by means of RNeasy Mini Kit (manufactured by QIAGEN). Using iScript cDNA Synthesis Kit (manufactured by BIO-RAD Laboratories, Inc.), cDNA was synthesized from the total RNA (200 ng). Using the cDNA as a template, Real-time PCR was carried out for analyzing the expression levels of S100A8 gene, β-defensin 1 gene, β-defensin 3 gene and β-defensin 14 gene (GAPDH gene as a reference). In the Real-time PCR analysis, SYBR Premix Ex Taq (manufactured by Takara Bio Inc.) was used and primers having the sequences shown in Table 1 were used. As a thermal cycler, Roche Light Cycler® 48011 was used. A cycle consisting of a holding step at 95° C. for 10 seconds, a reaction step at 95° C. for 10 seconds, a reaction step at 50° C. for 5 seconds and a reaction step at 72° C. for 10 seconds was repeated 50 times.

TABLE 1

|  | Forward | Reverse |
| --- | --- | --- |
| Gapdh | AACGACCCCTTCATTGAC (SEQ ID NO: 1) | TCCACGACATACTCAGCAC (SEQ ID NO: 2) |
| S100A8 | GGAAATCACCATGCCCTCTA (SEQ ID NO: 3) | GCTGTCTTTGTGAGATGCCA (SEQ ID NO: 4) |
| β-defensin 1 | CCAGATGGAGCCAGGTGTTG (SEQ ID NO: 5) | AGCTGGAGCGGAGACAGAATCC (SEQ ID NO: 6) |
| β-defensin 3 | GCATTGGCAACACTCGTCAGA (SEQ ID NO: 7) | CGGGATCTTGGTCTTCTCTA (SEQ ID NO: 8) |
| β-defensin 14 | TCTTGTTCTTGGTGCCTGCT (SEQ ID NO: 9) | CGACCGCTATTAGAACATCGAC (SEQ ID NO: 10) |

Skin pathological score and the number of living *Staphylococcus aureus* cells were analyzed by Mann-Whitney U-test; and antimicrobial gene expression in the ear was analyzed by Student's t-test. In this manner, significant difference between the *Lactococcus lactis* JCM5805 intake group and the standard diet intake group was analyzed.

<Results>

Figure 1:
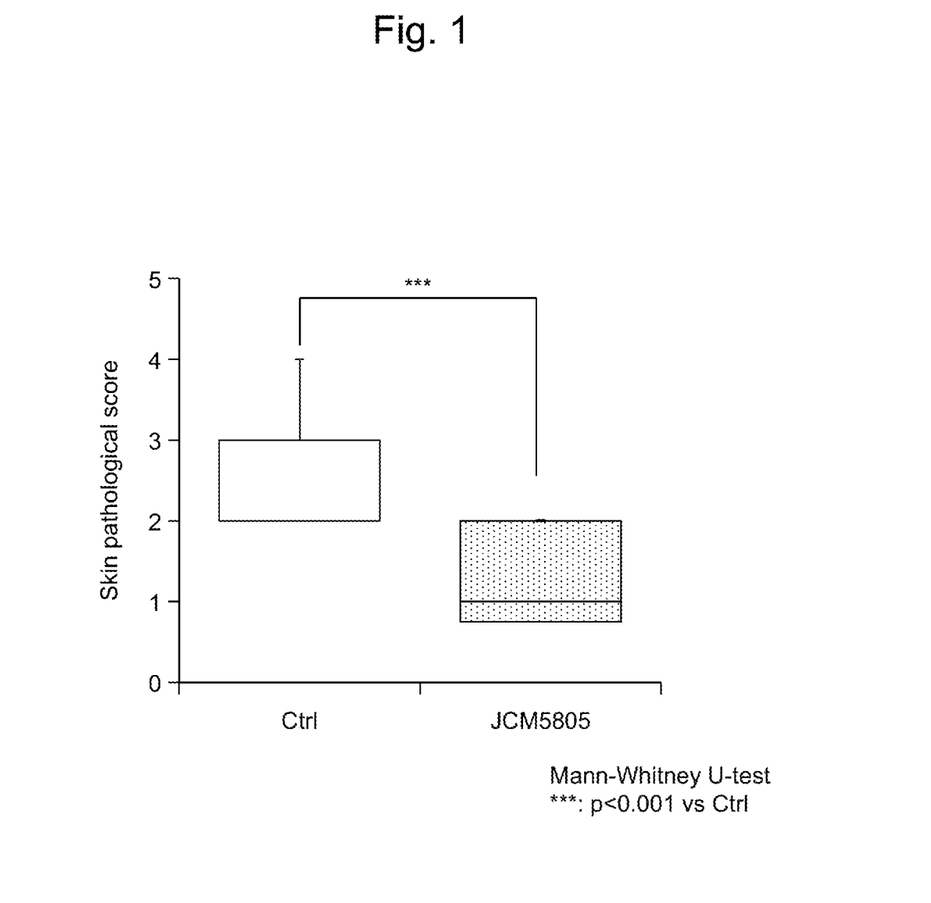
FIG. 1 shows the suppression effect of *Lactococcus lactis* JCM5805 on score of a pathological change caused by bacterial infection (2 days after infection).

As shown in FIG. 1, it was found that the score on severity of the skin pathological score caused by skin infection with *Staphylococcus aureus* is significantly low in the *Lactococcus lactis* JCM5805 intake group compared to the standard diet intake group. In other words, it was demonstrated that *Lactococcus lactis* JCM5805 has a reduction effect against exacerbation of a pathological change of the skin caused by *Staphylococcus aureus* infection.

Figure 2:
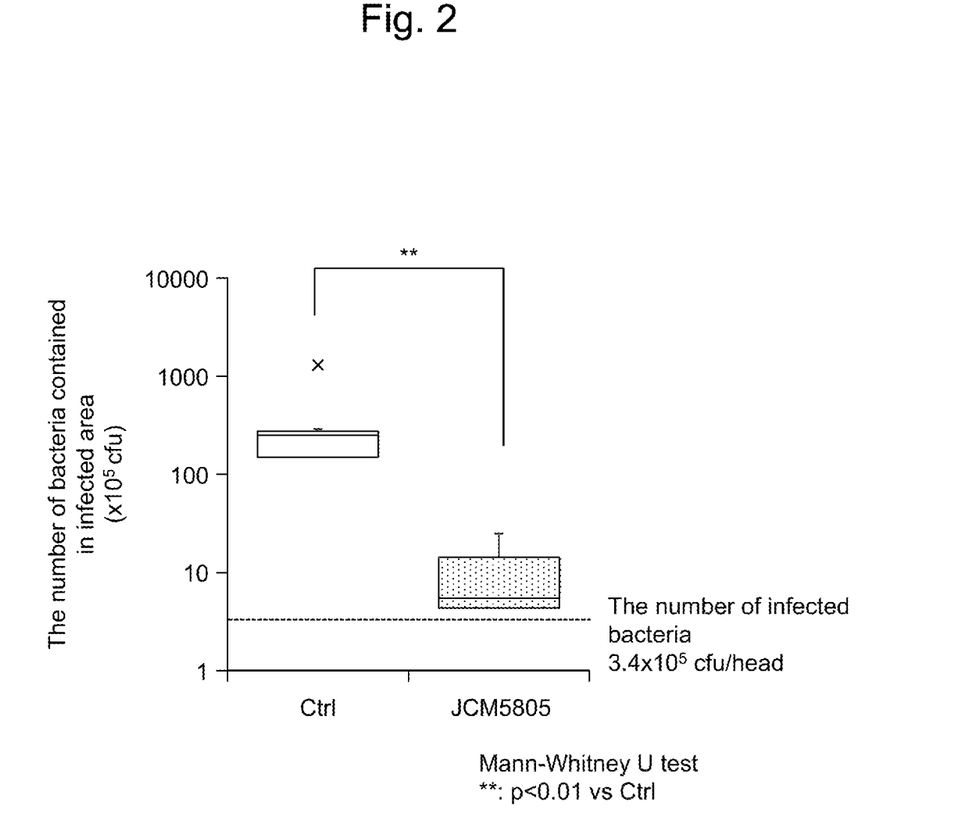
FIG. 2 shows the suppression effect of *Lactococcus lactis* JCM5805 on the number of living bacterial cells in an infected area (the number of bacterial cells in the infected area on 2 days after infection).

As shown in FIG. 2, it was found that the number of *Staphylococcus aureus* cells contained in the infection area is significantly low in the *Lactococcus lactis* JCM5805 intake group compared to the standard diet intake group. In other words, it was demonstrated that *Lactococcus lactis* JCM5805 has a suppression effect against growth of *Staphylococcus aureus* in the skin.

As shown in Table 2, average scores on all symptoms such as scab, epidermal thickening, pustule, intercellular edema and intracellular edema in the epidermis, and inflammatory cell infiltration in the dermis and subcutaneous tissue were low in the *Lactococcus lactis* JCM5805 intake group compared to the standard diet intake group. In other words, it was demonstrated that *Lactococcus lactis* JCM5805 has a suppression effect against exacerbation of a pathological change of the skin caused by *Staphylococcus aureus* infection.

TABLE 2

|  | Symptom | Average score of standard dietary intake group | Average score of JCM5805 intake group |
|---|---|---|---|
| Epidermis | Scab | 1.75 | 1 |
|  | Epidermal thickening | 2.5 | 1.875 |
|  | Pustule | 0.5 | 0 |
|  | Erosion/ulceration | 0.25 | 0 |
|  | Intercellular edema | 0.625 | 0.125 |
|  | Intracellular edema | 0.5 | 0 |
| Dermis | Inflammatory cell infiltration | 1.375 | 1 |
| Subcutaneous tissue | Inflammatory cell infiltration | 0.875 | 0.375 |

Figure 3:
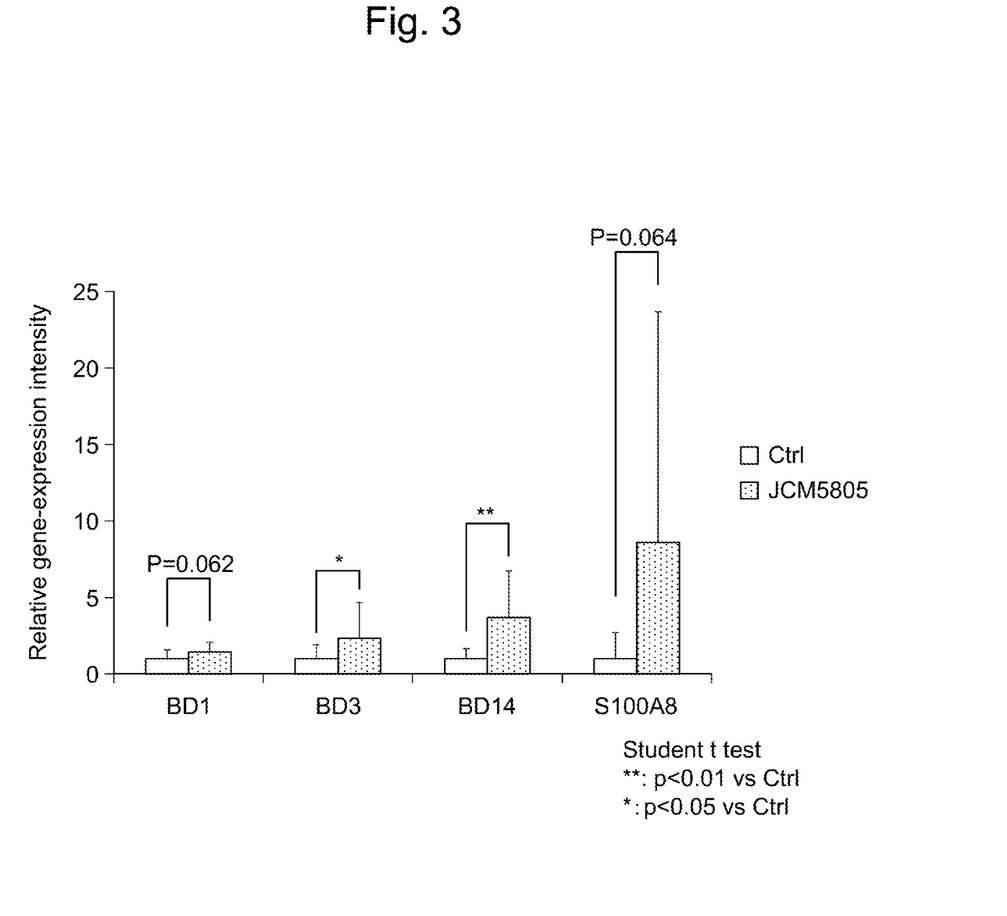
FIG. 3 shows expression of antibacterial genes in the skin (uninfected site) (2 days after infection).

As shown in FIG. 3, the expression levels of antibacterial genes such as β-defensin 3 gene and β-defensin 14 gene in the ear, i.e., a site not infected with *Staphylococcus aureus*, were significantly high in the *Lactococcus lactis* JCM5805 intake group compared to the standard diet intake group. Also, a tendency of the expression levels of S100A8 gene and β-defensin 1 gene to increase was observed. In other words, it was demonstrated that *Lactococcus lactis* JCM5805 has an augmentation effect on expression of antibacterial genes in the skin.

From the results, it was estimated that intake of *Lactococcus lactis* JCM5805 augments the expression of antimicrobial genes in the skin to suppress growth of bacterial cells in the skin infected with *Staphylococcus aureus*, with the result that exacerbation of various pathological changes of the skin caused by the infection can be suppressed.

[Example 3] Suppression Effect of *Lactococcus lactis* JCM5805 on Exacerbation of Pathological Change of the Skin Caused by *Staphylococcus aureus*

*Staphylococcus aureus* was inoculated in the skin of mice allowed to orally take *Lactococcus lactis* JCM5805 as shown in Example 2 and the severity of pathological score of the skin caused by infection was determined chronologically. In this manner, the protective effect against bacterial infection until the pathological change remitted was evaluated.

<Experimental Method>

BALB/C mice (5 weeks-old females, purchased from Japan SLC, Inc.) were divided into two groups each constituted of 3 mice. One was a standard diet intake group (AIN-930 diet). The other was a *Lactococcus lactis* JCM5805 intake group, which was fed AIN-93G, mixed with *Lactococcus lactis* JCM5805. The dosage amount of the lactic acid bacterium, administration method thereof and method for inoculating *Staphylococcus aureus* were the same as in Example 2, and the skin pathological score was evaluated from Day 0 to Day 6 after inoculation of *Staphylococcus aureus*.

In this Example, the skin pathological score may be sometimes referred to as a pathological-change score value or a pathological-change evaluation score.

After inoculation with *Staphylococcus aureus* suspension, individual mice were checked for papule and erosion of the infection area in accordance with the following 4 criteria: 0: asymptomatic, 1: mild, 2: moderate, 3: severe. The sum of evaluation scores on papule and erosion was used as a skin pathological score.

<Results>

Figure 4:
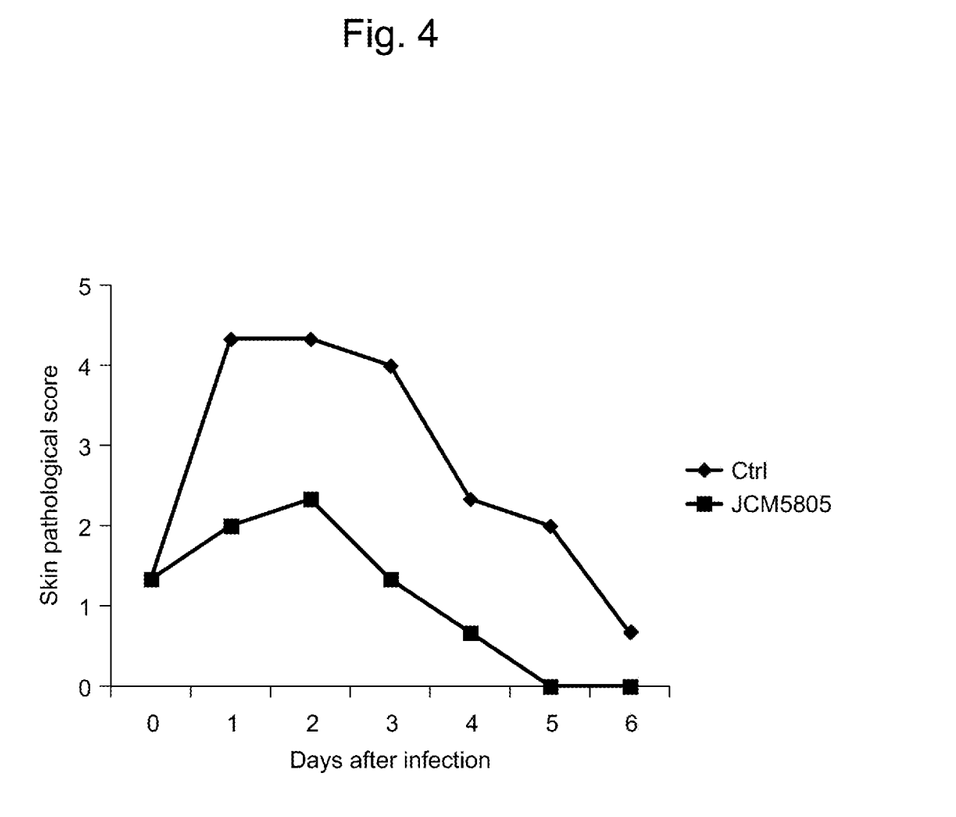
FIG. 4 shows the suppression effect of *Lactococcus lactis* JCM5805 on score of a pathological change caused by bacterial infection (chronological change).

FIG. 4 shows the skin pathological scores of the skin infected with *Staphylococcus aureus*. It was found that the *Lactococcus lactis* JCM5805 intake group shows low pathological-change evaluation score values at all time points, compared to the standard diet intake group.

From the above, it was demonstrated that *Lactococcus lactis* JCM5805 has a suppression effect on exacerbation of a pathological change of the skin induced by skin infection with *Staphylococcus aureus*.

Example 4

Antibacterial Activity Against *Staphylococcus aureus* on the Skin by Intake of *Lactococcus lactis* JCM5805

The antibacterial activity against *Staphylococcus aureus* of an extract from the skin of a mouse allowed to orally take *Lactococcus lactis* JCM5805 was compared to that of a mouse allowed to take a standard diet.

<Experimental Method>

BALB/C mice (7 weeks-old females, purchased from Charles River Laboratories Japan, Inc.) were divided into two groups each constituted of 8 mice. One was a standard diet intake group (AIN-93G diet). The other was a *Lactococcus lactis* JCM5805 intake group, which was fed AIN-93G mixed with *Lactococcus lactis* JCM5805. The dosage amount of the lactic acid bacterium was 1 mg per mouse per day. The day on which administration of lactic acid bacterium was initiated was determined as Day 0. On Day 14, mice were dissected to obtain dorsal skin.

The dorsal skin was disrupted with a cell disruptor for multiple specimens, Multi-Beads Shocker® (manufactured by Yasui Kikai Corporation). To a disrupted sample, RIPA buffer (manufactured by Thermo Fisher Scientific) was added. The mixture was stirred at room temperature for 5 minutes and centrifuged as 10,000×g for 5 minutes. The supernatant was recovered to obtain a skin extract. The concentration of a protein in the skin extract was measured by BCA Protein Quantitation kit (manufactured by Thermo Fisher Scientific).

(1) Antibacterial effect of the skin extract against *Staphylococcus aureus* was evaluated. *Staphylococcus aureus* MW2 strain was cultured in a nutrient broth medium. An aliquot corresponding to 1×10$^7$ CFU was taken from the medium and the suspending solution was exchanged with 5 mM MOPS buffer (pH 6.8) (manufactured by Dojindo Laboratories). To the bacterial suspension, the mouse skin extract prepared above was added so as to obtain a concentration of 5 µg/mL. The mixture was cultured at 37° C. for 4 hours. After culture for 4 hours, the bacterial suspension was appropriately diluted (100 fold or 1000 fold with a medium) and seeded on a nutrient broth agar plate by means of a spiral plater (manufactured by IUL Instruments). After culture was carried out at 37° C. for 24 hours, the number of colonies was determined by an automatic colony counter, aCOLyte (manufactured by Synbiosis), and the number of bacterial cells was determined.

(2) Antibacterial effect of the skin extract against *Staphylococcus epidermidis* was evaluated. *Staphylococcus epidermidis* JCM12993 strain was cultured in a nutrient broth medium. An aliquot corresponding to 1×10$^7$ CFU was taken from the medium and the suspending solution was exchanged with 5 mM MOPS buffer (pH 6.8). To the bacterial suspension, the mouse skin extract prepared above was added so as to obtain a concentration of 5 µg/mL. The mixture was cultured at 37° C. for 4 hours. After culture for 4 hours, the bacterial suspension was appropriately diluted (100 fold or 1000 fold with a medium) and seeded on an ordinary bouillon agar medium by means of a spiral plater. After culture was carried out at 37° C. for 24 hours, the number of colonies was determined by aCOLyte and the number of bacterial cells was determined.

(3) Antibacterial effect of the skin extract against *Propionibacterium acnes* was evaluated. *Propionibacterium acnes* JCM6425 strain was cultured in brain heart infusion medium (manufactured by Eiken Chemical Co., Ltd.). An aliquot corresponding to 1×10$^6$ CFU was taken from the medium and the suspending solution was exchanged with 5 mM MOPS buffer (pH 6.8). To the bacterial suspension, the mouse skin extract prepared above was added so as to obtain a concentration of 5 µg/mL. The mixture was cultured at 37° C. for 4 hours. After culture for 4 hours, the bacterial suspension was appropriately diluted (100 fold or 1000 fold with a medium) and seeded on a brain heart infusion agar plate by means of a spiral plater. After culture was carried out at 37° C. for 24 hours, the number of colonies was determined by aCOLyte and the number of bacterial cells was determined.

The number of bacterial cells determined was analyzed by Student's t-test to obtain significant difference between the *Lactococcus lactis* JCM5805 intake group and the standard dietary intake group.

<Results>

Figure 5:
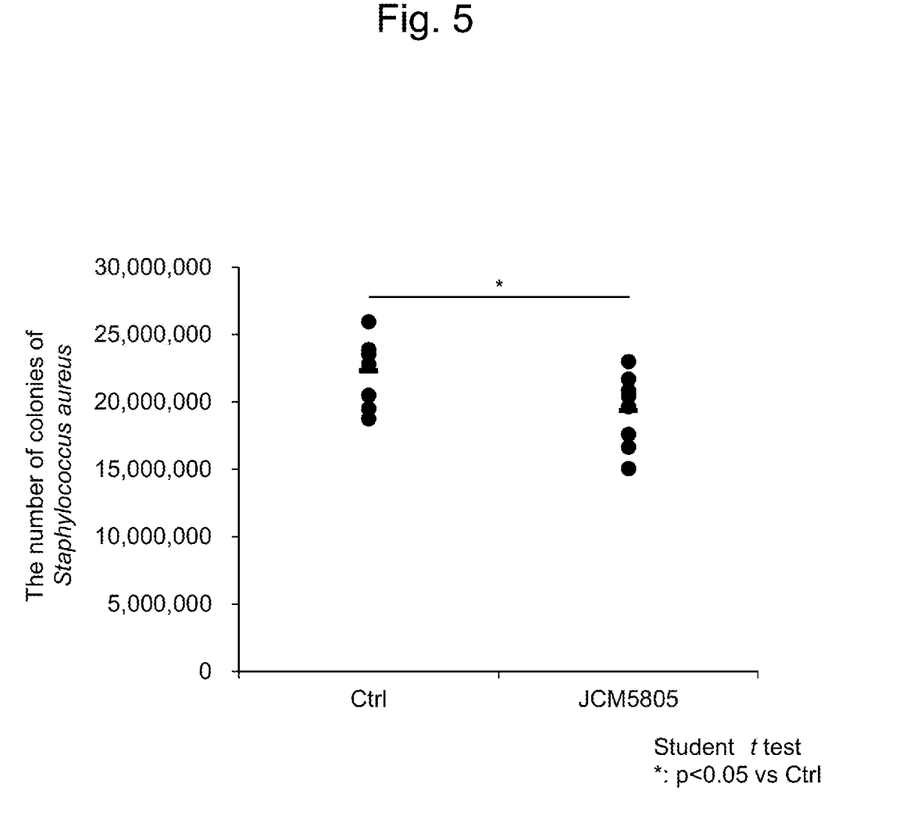
FIG. 5 shows the antibacterial activity against *Staphylococcus aureus* in the skin when *Lactococcus lactis* JCM5805 was taken.

As shown in FIG. 5, it was apparent that the number of bacterial cells of *Staphylococcus aureus* MW2 strain is significantly low in the *Lactococcus lactis* JCM5805 intake group compared to the standard diet intake group and demonstrated that the antibacterial effect is enhanced.

Figure 6:
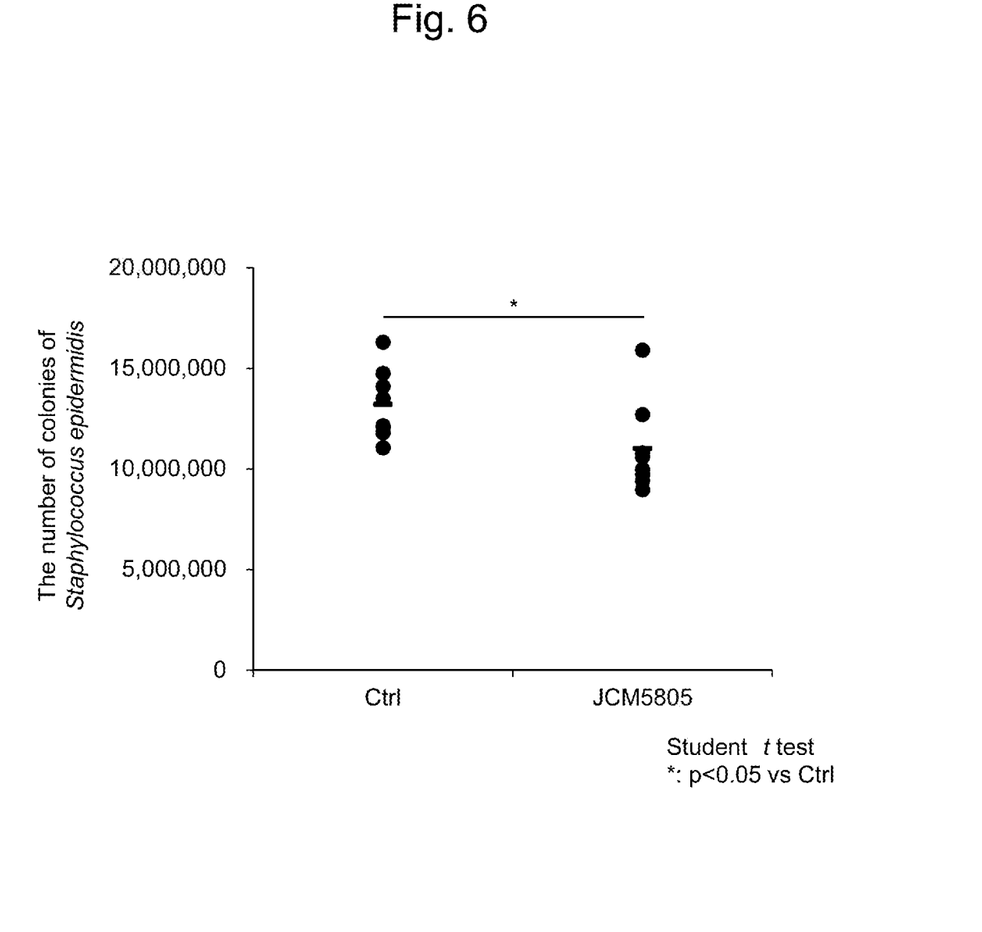
FIG. 6 shows the antibacterial activity against *Staphylococcus epidermidis* in the skin when *Lactococcus lactis* JCM5805 was taken.

As shown in FIG. 6, it was apparent that the number of bacterial cells of *Staphylococcus epidermidis* JCM12993 strain is significantly low in the *Lactococcus lactis* JCM5805 intake group compared to the standard diet intake group and demonstrated that the antibacterial effect is enhanced.

Figure 7:
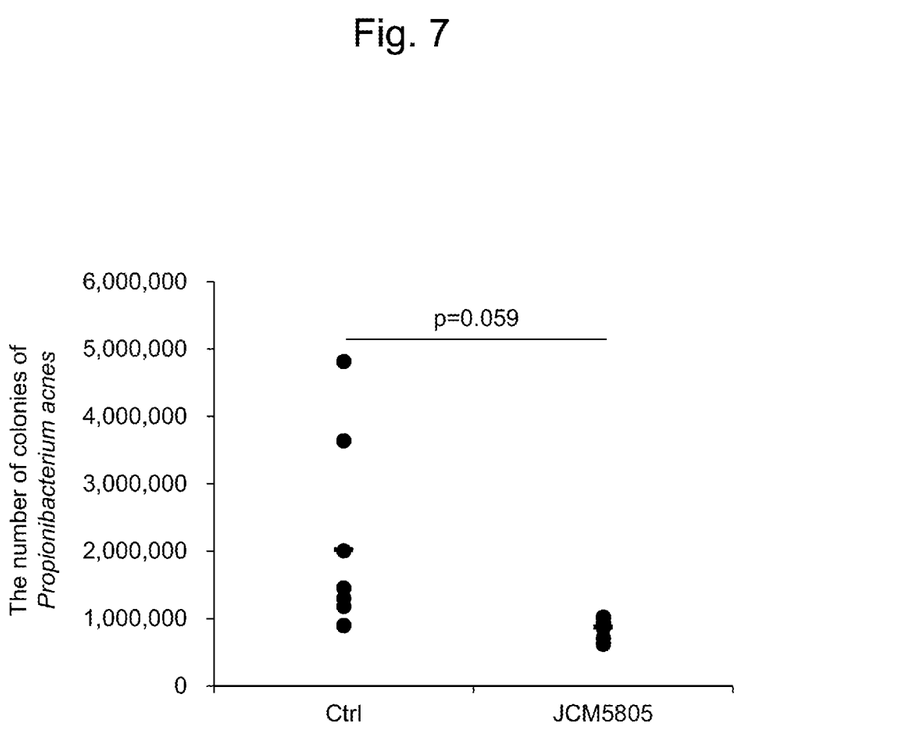
FIG. 7 shows the antibacterial activity against *Propionibacterium acnes* in the skin when *Lactococcus lactis* JCM5805 was taken.

As shown in FIG. 7, it was apparent that the number of cells of *Propionibacterium acnes* JCM6425 strain is significantly low in the *Lactococcus lactis* JCM5805 intake group compared to the standard diet intake group and demonstrated that the antibacterial effect is enhanced.

From the results, it was apparent that the expression of antimicrobial gene s of the skin was augmented by intake of *Lactococcus lactis* JCM5805, and antibacterial activities against not only *Staphylococcus aureus* but also representative skin resident bacteria that deteriorate the condition of skin if they are abnormally grown, are augmented.

All publications, patents and patent applications cited in the specification are incorporated herein in their entirety by reference.

INDUSTRIAL APPLICABILITY

The lactic acid bacterium of the present invention that can prevent or improve deterioration of skin condition caused by infection of a specific bacterium, can be used as an active ingredient of medical drugs, functional foods and specified health foods or drinks.

The invention claimed is:

1. A method for suppressing abnormal bacterial growth in the skin, or preventing or ameliorating deterioration of a skin condition caused by abnormal bacterial growth, comprising administering orally an effective amount of a composition comprising *Lactococcus lactis* JCM5805 cells as an active ingredient to a human subject in need thereof, wherein the *Lactococcus lactis* JCM5805 cells comprise dead cells, disrupted cells, lyophilized cells, cells obtained from a culture solution, cells obtained from a culture-solution extract, treated cells, or a combination thereof, and wherein the abnormal bacterial growth is from a bacterium selected from the group consisting of *Staphylococcus aureus, Staphylococcus epidermidis*, and rod-shape acne.

2. The method according to claim 1, wherein the rod-shape acne is *Propionibacterium acnes*.

3. The method according to claim 1, wherein the composition is a food composition.

4. The method according to claim 1, wherein the composition is a pharmaceutical composition.

5. The method according to claim 3, wherein the skin condition caused by the abnormal bacterial growth is dermatitis.

6. The method according to claim 4, wherein the skin condition caused by the abnormal bacterial growth is selected from the group consisting of impetigo contagiosa, cellulitis, erysipelas, staphylococcal scalded skin syndrome, folliculitis, acne, furuncle, carbuncle, bacterial perionychium inflammation, chronic pyoderma, and sycosis vulgaris.

7. The method according to claim 4, wherein the skin condition caused by the abnormal bacterial growth is dermatitis.

8. A method of promoting expression of at least one antibacterial gene in the skin of a subject, comprising orally administering to a subject in need thereof an effective amount of a composition comprising *Lactococcus lactis* JCM5805 cells, wherein the *Lactococcus lactis* JCM5805 cells comprise live cells, dead cells, disrupted cells, lyophilized cells, or a combination thereof, and wherein the at least one antibacterial gene is selected from β-defensin 1 (BD-1), β-defensin 3 (BD-3), β-defensin 14 (BD-14), and S100A8.

9. The method according to claim 8, wherein the subject has a skin condition caused by abnormal bacterial growth.

10. The method according to claim 9, wherein the abnormal bacterial growth is from a bacterium selected from the group consisting of *Staphylococcus aureus, Staphylococcus epidermidis*, and rod-shape acne.

11. The method according to claim 9, wherein the skin condition caused by the abnormal bacterial growth is dermatitis.

12. The method according to claim 9, wherein the skin condition caused by the abnormal bacterial growth is selected from the group consisting of impetigo contagiosa, cellulitis, erysipelas, staphylococcal scalded skin syndrome, folliculitis, acne, furuncle, carbuncle, bacterial perionychium inflammation, chronic pyoderma, and sycosis vulgaris.

13. The method according to claim 8, wherein the composition is a food composition.

14. The method according to claim 8, wherein the composition is a pharmaceutical composition.

15. The method according to claim 8, wherein the at least one antibacterial gene comprises at least two genes selected from β-defensin 1 (BD-1), β-defensin 3 (BD-3), β-defensin 14 (BD-14), and S100A8.

16. The method according to claim 8, wherein the at least one antibacterial gene comprises all of β-defensin 1 (BD-1), β-defensin 3 (BD-3), β-defensin 14 (BD-14), and S100A8.

* * * * *